(12) United States Patent
Wenz

(10) Patent No.: US 7,758,693 B2
(45) Date of Patent: *Jul. 20, 2010

(54) STRONTIUM-APATITE CEMENT PREPARATIONS, CEMENTS FORMED THEREFROM, AND USES THEREOF

(75) Inventor: Robert Wenz, Wollstadt (DE)

(73) Assignee: Kyphon Sarl (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/359,907

(22) Filed: Jan. 26, 2009

(65) Prior Publication Data

US 2009/0131949 A1 May 21, 2009

Related U.S. Application Data

(63) Continuation of application No. 11/851,346, filed on Sep. 6, 2007, now Pat. No. 7,501,020, which is a continuation of application No. 11/006,326, filed on Dec. 6, 2004, now Pat. No. 7,273,523, which is a continuation-in-part of application No. PCT/EP03/05059, filed on May 14, 2003.

(30) Foreign Application Priority Data

Jun. 7, 2002 (DE) ............................... 102 25 420

(51) Int. Cl.
A61L 27/44 (2006.01)
A61K 31/75 (2006.01)
A61K 33/06 (2006.01)
A61K 33/08 (2006.01)

(52) U.S. Cl. .................... 106/690; 106/691; 623/23.62; 623/16.11

(58) Field of Classification Search .............. 623/23.62, 623/16.11; 106/690, 691
See application file for complete search history.

(56) References Cited

U.S. PATENT DOCUMENTS

| 3,746,680 | A | 7/1973 | Boricheski |
| 4,141,864 | A | 2/1979 | Rijke et al. |
| 4,192,021 | A | 3/1980 | Deibig et al. |
| 4,239,113 | A | 12/1980 | Gross et al. |
| 4,341,691 | A | 7/1982 | Anuta |
| 4,404,327 | A | 9/1983 | Crugola et al. |
| 4,518,430 | A | 5/1985 | Brown et al. |
| 4,588,583 | A | 5/1986 | Pietsch et al. |
| 4,612,053 | A | 9/1986 | Brown et al. |
| 4,629,464 | A | 12/1986 | Takata et al. |
| 4,668,295 | A * | 5/1987 | Bajpai ................. 106/690 |
| 4,678,436 | A | 7/1987 | Kondo et al. |
| 4,722,948 | A | 2/1988 | Sanderson |
| 4,791,150 | A | 12/1988 | Braden et al. |
| 4,872,936 | A | 10/1989 | Engelbrecht |
| 4,902,649 | A | 2/1990 | Kimura et al. |
| 4,940,689 | A | 7/1990 | Ito |
| 4,957,352 | A | 9/1990 | Yasuda et al. |
| 4,959,104 | A | 9/1990 | Iino et al. |
| 5,004,501 | A | 4/1991 | Faccioli et al. |
| 5,108,956 | A | 4/1992 | Inoue et al. |
| 5,149,368 | A * | 9/1992 | Liu et al. ................ 424/602 |
| 5,160,371 | A | 11/1992 | Ito |
| 5,171,720 | A | 12/1992 | Kawakami |
| 5,179,065 | A | 1/1993 | Ito |
| 5,204,382 | A | 4/1993 | Wallace et al. |
| 5,205,928 | A | 4/1993 | Inoue et al. |
| 5,226,877 | A | 7/1993 | Epstein |
| 5,262,166 | A | 11/1993 | Liu et al. |
| 5,276,070 | A | 1/1994 | Arroyo |
| 5,281,265 | A | 1/1994 | Liu |
| 5,352,715 | A | 10/1994 | Wallace et al. |
| 5,462,356 | A | 10/1995 | Murray |
| 5,462,722 | A | 10/1995 | Liu et al. |
| 5,522,893 | A | 6/1996 | Chow et al. |
| 5,545,254 | A | 8/1996 | Chow et al. |
| 5,605,713 | A | 2/1997 | Boltong |
| 5,650,108 | A | 7/1997 | Nies et al. |
| 5,695,729 | A | 12/1997 | Chow et al. |
| 5,795,922 | A | 8/1998 | Demian et al. |
| 5,797,873 | A | 8/1998 | Franz et al. |
| 5,814,683 | A | 9/1998 | Branham |
| 5,847,046 | A | 12/1998 | Jiang et al. |

(Continued)

FOREIGN PATENT DOCUMENTS

DE 29607832 10/1996

(Continued)

OTHER PUBLICATIONS

Brown, W., et al., "A new calcium phosphate, water-setting cement," *Chem. Res. Prog.*, pp. 352-379 (1986).

(Continued)

*Primary Examiner*—C. Melissa Koslow

(57) ABSTRACT

Calcium-strontium-hydroxyphosphate (strontium-apatite-) cement preparations are described, comprising a powder mixture, which contains molar quantities of the components calcium (Ca), strontium (Sr) and phosphate (P) in the mixture in the ranges $1.00 < Ca/P \leq 1.50$ and $0 < Sr/P < 1.5$, together with an alkali salt or an ammonium salt of phosphoric acid, and with water and/or an aqueous solution. The powder mixture particularly contains, as the Ca-component, $Ca_3(PO_4)_2$ (TCP), and as the Sr-component $SrHPO_4$ and/or $Sr_3(PO_4)_2$ and optionally additional $SrCO_3$. As the aqueous mixing solution for the formation of the strontium-apatite cement, an aqueous solution of an alkali salt or an ammonium salt of the phosphoric acid is suitable.

18 Claims, No Drawings

U.S. PATENT DOCUMENTS

| | | | |
|---|---|---|---|
| 5,914,356 A | 6/1999 | Erbe | |
| 5,952,010 A | 9/1999 | Constantz | |
| 6,002,065 A | 12/1999 | Constantz et al. | |
| 6,075,067 A | 6/2000 | Lidgren | |
| 6,124,373 A | 9/2000 | Peter et al. | |
| 6,153,664 A | 11/2000 | Wise et al. | |
| 6,187,046 B1 | 2/2001 | Yamamoto et al. | |
| 6,203,574 B1 | 3/2001 | Kawamura | |
| 6,206,957 B1* | 3/2001 | Driessens et al. | 106/35 |
| 6,224,635 B1 | 5/2001 | Ricci et al. | |
| 6,231,615 B1 | 5/2001 | Preissman | |
| 6,241,734 B1 | 6/2001 | Scribner et al. | |
| 6,248,110 B1 | 6/2001 | Reiley et al. | |
| 6,273,916 B1 | 8/2001 | Murphy | |
| 6,309,420 B1 | 10/2001 | Preissman | |
| 6,325,992 B1 | 12/2001 | Chow et al. | |
| 6,338,810 B1 | 1/2002 | Carpena et al. | |
| 6,436,143 B1 | 8/2002 | Ross et al. | |
| 6,497,901 B1 | 12/2002 | Royer | |
| 6,521,264 B1 | 2/2003 | Lacout et al. | |
| 6,547,866 B1 | 4/2003 | Edwards et al. | |
| 6,562,755 B1 | 5/2003 | Halbrook, Jr. et al. | |
| 6,593,394 B1 | 7/2003 | Li et al. | |
| 6,613,054 B2 | 9/2003 | Scribner et al. | |
| 6,692,563 B2 | 2/2004 | Zimmermann | |
| 6,908,506 B2 | 6/2005 | Zimmermann | |
| 6,953,594 B2 | 10/2005 | Lee et al. | |
| 6,994,726 B2 | 2/2006 | Lin et al. | |
| 7,008,433 B2 | 3/2006 | Voellmicke et al. | |
| 7,115,163 B2 | 10/2006 | Zimmermann | |
| 7,135,027 B2 | 11/2006 | Delmotte | |
| 7,138,442 B2 | 11/2006 | Smith et al. | |
| 7,160,932 B2 | 1/2007 | Schilke et al. | |
| 7,273,523 B2* | 9/2007 | Wenz | 106/690 |
| 7,501,020 B2* | 3/2009 | Wenz | 106/690 |
| 2001/0012968 A1 | 8/2001 | Preissman | |
| 2002/0152929 A1 | 10/2002 | Burgath et al. | |
| 2002/0167480 A1 | 11/2002 | Johnson et al. | |
| 2002/0187104 A1 | 12/2002 | Li et al. | |
| 2002/0191487 A1 | 12/2002 | Sand | |
| 2003/0031698 A1 | 2/2003 | Roeder et al. | |
| 2003/0032964 A1 | 2/2003 | Watkins et al. | |
| 2003/0055512 A1 | 3/2003 | Genin et al. | |
| 2003/0139488 A1 | 7/2003 | Wojciak | |
| 2003/0161858 A1 | 8/2003 | Lidgren | |
| 2003/0180344 A1 | 9/2003 | Wise et al. | |
| 2004/0048947 A1 | 3/2004 | Lidgren et al. | |
| 2004/0122359 A1 | 6/2004 | Wenz et al. | |
| 2004/0157952 A1 | 8/2004 | Soffiati et al. | |
| 2004/0226479 A1 | 11/2004 | Lyles et al. | |
| 2004/0265385 A1 | 12/2004 | West | |
| 2005/0105384 A1 | 5/2005 | Eder et al. | |
| 2005/0142211 A1 | 6/2005 | Wenz | |
| 2005/0199156 A1 | 9/2005 | Khairoun et al. | |
| 2005/0246036 A1 | 11/2005 | Zimmermann | |
| 2005/0256220 A1 | 11/2005 | Lavergne et al. | |
| 2006/0079905 A1 | 4/2006 | Beyar et al. | |
| 2007/0021526 A1 | 1/2007 | He et al. | |
| 2007/0032567 A1 | 2/2007 | Beyar et al. | |
| 2007/0048382 A1 | 3/2007 | Meyer et al. | |
| 2007/0128245 A1 | 6/2007 | Rosenberg et al. | |
| 2007/0191964 A1 | 8/2007 | Preissman | |
| 2007/0254011 A1 | 11/2007 | Schnabelrauch et al. | |

FOREIGN PATENT DOCUMENTS

| | | |
|---|---|---|
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 543765 * | 5/1993 |
| EP | 0543765 A1 | 5/1993 |
| EP | 0835668 A1 | 4/1998 |
| EP | 1002513 A1 | 5/2000 |
| EP | 1255576 B1 | 8/2003 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0202478 A1 | 1/2002 |
| WO | WO0232827 A1 | 4/2002 |
| WO | WO0236518 A1 | 5/2002 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |

OTHER PUBLICATIONS

Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-1086 (2004) (abstract only).

Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).

Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).

Bezzi G. et al., A novel sol-gel technique for hydroxyapatite preparation, Materials Chemistry and Physics, 2003, 78: 816-824, entire document.

Bonfield et al., Hydroxyapatite Composite Biomaterials—Evolution and Applications, Materials World, vol. 5, No. 1, pp. 18-20 (1997).

Canul-Chuil et al., Comparative Study of Bone Cements prepared with either HA or alpha-TCP and Functionalized Methacrylates, J Biomed Mater Res, vol. 64B, No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-4 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Ishikawa et al., Effects of neutral sodium hydrogen phosphate on setting reaction and mechanical strength of hydroxyapatite putty, J Biomed Mater Res, 44, 322-329, 1999.

Ishikawa et al., Non-decay type fast-setting calcium phosphate cement Hydroxyapatite putty containing an increased amount of sodium alginate, J Biomed Mater Res, 36, 393-399, 1997.

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-70 (2000) (abstract only).

Liu et al., Influence of the Aspect Ratio of Bioactive Nanofillers on Rheological Behavior of PMMA-Based Orthopedic Materials, J Biomed Mater Res, vol. 71 B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

The term "PRE-", Merriam-Webster Online Dictionary, at the web: http://www.m-w.com , p. 1-2.

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).

Wong et al., Ultrastructural Study of Mineralization of a Strontium-Containing Hydroxyapatite (Sr-HA) Cement In Vivo, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).

International Search Report, WIPO, Jan. 22, 2009.

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

Heini, P.F., et al., "Bone substitutes in vertebroplasty," *Eur. Spine J.*, Jun. 14, 2001, vol. 10, pp. S205-S213.

Li, Y., et al. "Preparation of amorphous calcium phosphate in the presence of poly(ethylene glycol)," *Journal of Materials Science Letters*, 2003, vol. 22, pp. 1015-1016.

* cited by examiner

STRONTIUM-APATITE CEMENT PREPARATIONS, CEMENTS FORMED THEREFROM, AND USES THEREOF

CROSS-REFERENCES TO RELATED APPLICATIONS

This application is a continuation of U.S. patent application Ser. No. 11/851,346, filed Sept. 6, 2007, now U.S. Pat. No. 7,501,020, which is a continuation of U.S. patent application Ser. No. 11/006,326, filed Dec. 6, 2004, now U.S. Pat. No. 7,273,523, which is a continuation-in-part of PCT/EP03/05059, which designated the United States, filed on May 14, 2003, which claimed the benefit of German application No. 10225420.6, filed on Jun. 7, 2002, the full disclosures of which are incorporated herein by reference.

BACKGROUND OF THE INVENTION

The invention relates to calcium-strontium-hydroxyphosphate-(strontium-apatite-) cement preparations, which contain calcium and strontium, and to uses thereof. The invention further relates to strontium-apatite cements, which are formed from these cement preparations, and to a process applied for their manufacture. The strontium-apatite is well suitable for medical purposes, in particular as bone substitute materials, with specific suitability for filling bone defects caused by osteoporosis.

The human and animal hard tissue essentially consists of hydroxyapatite, wherein there is mostly no stoichiometric hydroxyapatite, but an apatite structure, in which sodium- (Na), potassium- (K), magnesium- (Mg) and strontium- (Sr) salts are further incorporated.

In addition, carbonate, that is incorporated into the apatite structure by substituting phosphate groups, is further incorporated into the hard tissue.

Physiologically occurring apatite is nanocrystalline, illustrated in the X-ray diffractogram in the form of a band broadening, which does not allow an exact allocation of the apatite structures, as it is rather a superposition of single peaks.

Calcium phosphates are biocompatible and osteoconductive, which means that newly formed bone tissue deposits directly thereon. In addition, they are resorbable, because they are recognized as body-consistent (i.e., the body recognizes them as part of itself) and can be catabolized by specific bone-resorbing cells such as osteoclasts, within the framework of natural bone metabolism and restructuring. During such restructuring processes, calcium phosphates can be catabolized and substituted by endogenous bones.

Calcium phosphate ceramics have been on the market since about 1970. They are predominantly incorporated into the human and animal body in the form of pre-made molded bodies or as granules. These materials proved to be effective in clinical applications, however, they can be incorporated only rarely into defects in a force-fit manner, since the defects are mostly irregular. Failure to provide a force-fit incorporation, however, often results in a washing-out of the granules, or in an in-growth of connective tissue into the defects. This subsequently leads to a failure of augmentation.

Calcium phosphate ceramics are predominantly prepared from hydroxyapatite, whereby these ceramics are not resorbable, or from bi-phasic calcium phosphate ceramics, which consist of varying proportions of β-tricalcium phosphate (β-TCP) and hydroxyapatite and which may be resorbed due to the resorbability of the β-tricalcium phosphate, corresponding to its mass proportion.

Calcium phosphate cements have been mentioned in the literature since 1985. They have advantages over ceramics, because they can be incorporated force-fit into the body (W. E. Brown and L. C. Chow, "A new calcium phosphate, water-setting cement", Chem. Res. Prog. (1986) 352-379; U.S. Pat. No. 4,612,053; U.S. Pat. No. 5,149,368; U.S. Pat. No. 4,518,430; WO96/14265; EP0835668A1). These cements are characterized by a calcium/phosphate (Ca/P) ratio of $\geq 1.5$.

By adding carbonate, this ratio can be increased even further. There are contradictory reports about the resorbability of these materials, because such cements can not be resorbed, if the reaction product is hydroxyapatite. Or, if the reaction product is calcium-deficient hydroxyapatite (CDHA), it is resorbable by osteoclasts and can be substituted with new bone by means of osteoblasts. However, the resorption rate is then not predictable, because the resorption is dependent on the cellular activity of the recipient, the local blood flow rate, and the location of the implant.

Such cements have already been successfully introduced into the market (BoneSource® cement, Norian® SRS® cement, Biobon® cement, Calcibon® cement). A main point of criticism from the user's view, however, is still the unpredictable resorbability. The market demands a product, which ensures a high mechanical stability, and which is eventually completely resorbed. After a certain period of time, the product should be substituted with endogenous bone material. Thus, many manufacturers add soluble minerals such as $CaHPO_4$, $CaSO_4$, $CaCO_3$ or β-TCP to the bone substitute materials, in order to enhance the resorption rate in addition to the passive solubility. However, this solves the problem only partially, because the main component still remains only slightly resorbable or not at all resorbable.

The cement resorption, which is essentially controlled by cellular phenomena, follows the rules of Wolff's Law. Wolff's Law describes the steady bone restructuring conditions, and its main assertion is that bone remains only at locations where it is indeed required from a bio-mechanical point of view. From this assertion, it follows that the pressure strength of an artificial bone substitute material should be directed by that of trabecular bone.

This means that a pressure strength of >40 MPa is not desirable at all, because otherwise a certain "stress-shielding" is generated by the cement, which loosens up the bone structure of the adjacent implant bearing due to the higher strength of the cement. Thereby, the place of the lowest bio-mechanical strength of the cement is shifted to the periphery of the implant bearing, which is not desirable.

The main use of bone substitute materials lies in the filling of metaphysic bone defects and of vertebral bodies. These defects mainly occur during osteoporosis. Osteoporosis is a systemic disease of the whole organism, which is essentially expressed by an imbalance of the bone metabolism. Here, the anabolic and catabolic bone restructuring processes are reversed, and more bone material is decomposed by an osteoclastic activity, than is grown by the osteoblastic activity. Attempts to control this imbalance of bone decomposition rate to bone growth rate have been to deliver various systemically effective substances. These include, inter alia, bisphosphonates and hormone preparations, which however threaten the whole organism. In this respect, a bone substitute material that would be desirable is characterized by not only representing a bone substitute substance or filler, but a material that acts upon the surrounding bone cells in such a way that it reverses the metabolic processes, so that the excessive osteoclastic activity itself is attenuated by the bone substitute material and the osteoblastic activity (the in-growth of bones) is stimulated. The aim is to avoid the development that, once a bone substitute material is incorporated through the osteoblastic activity, it is again rapidly decomposed by the increased osteoclastic activity, without the ability of building up new bone at the same time due to the attenuation of osteoblastic activity caused by osteoporosis.

These problems are not solved when considering the present state of the art. In WO92/02478 A1 a calcium phosphate cement containing strontium ions in the form of $SrCO_3$ is disclosed, however, the strontium carbonate is only used for influencing the expansion properties of the cement which, as a main component, consists of magnesium ammonium phosphate. In addition, this strontium carbonate is dissolved rapidly out of the cement due to its potential solubility, so that no protracting effect can originate therefrom, and thereby the bone metabolism cannot be influenced.

It would therefore be desirable to provide a material, which is particularly suitable as a bone substitute material, particularly for osteoporotic bone.

BRIEF SUMMARY OF THE INVENTION

Cement preparations according to the invention comprise calcium and strontium ions. The calcium and strontium ions can be incorporated into the preparations as phosphates or hydrogenphosphates, or optionally carbonates. Natural sources (e.g., calcium phosphates) may not be pure and may contain contaminating trace amounts of magnesium. In the present invention, however, magnesium ions are preferably absent or present only in insignificant amounts, such as unavoidable traces (i.e., magnesium ions are of insufficient quantity to substantially inhibit the formation of a strontium-apatite structure).

Due to their composition, the cement preparations of the present invention, and the hardened strontium-apatite materials resulting therefrom, can provide a prolonged release of strontium ions. It is thus possible to improve bone metabolism in osteoporotic bones, particularly by generating anabolic activity of the bone metabolism in the osteoporotic bone. A permanent stimulation of the osteoblastic activity may be achieved in osteoporotic bone, while at the same time the osteoclastic activity (which is elevated in osteoporotic bone) is inhibited.

The present invention further provides a cement system for filling bone defects in a form-fit manner where the cement preparations are hardenable not only at room temperature, but also at body temperature, and are workable by the user for a sufficiently long period. After full hardening, cement preparations according to the invention will have sufficiently high pressure strength in the human or animal body. The calcium-strontium-hydroxyphosphate (strontium-apatite) formed from the cement preparation is nanocrystalline and achieves its maximal strength in a period of a few hours up to a few days.

The cement preparations of the invention may, depending on the biological environment, be biologically degradable or resorbable within the body. The materials according to the invention exhibit good cohesion ability when contacted with body fluids. The materials according to the invention will also have higher water solubility than calcium-deficient hydroxyapatite, such that the favorable solubility promotes replacement of endogenous bone.

Thus, the materials provided by the present invention are suitable not only for closing bone defects, but also for promoting anabolic activity in the bone, and thus can contribute actively to the bone anabolism.

DETAILED DESCRIPTION OF THE INVENTION

The cement preparations of the present invention comprise a powder mixture having a molar calcium-to-phosphate (Ca/P) ratio in the range from about 1 to about 1.5 and a molar strontium-to-phosphate (Sr/P) ratio which does not exceed (i.e., not greater than about) 1.5. The molar Sr/P ratio is preferably at least 0.2 and further preferably at least 0.5. In a preferred embodiment, the phosphate is orthophosphate.

The cement preparation according to the invention can be determined by the chemical composition of the starting components for the formation of the strontium-apatite cement and contains, as minimum components in the powder mixture, at least $SrHPO_4$ and/or $Sr_3(PO_4)_2$, and optionally additional $SrCO_3$ besides $Ca_3(PO_4)_2$ (TCP), which may be present as α- and/or β-TCP.

The subsequent description relates to both aspects of the invention.

The alkali salt or ammonium salt of the phosphoric acid may be present, as starting material of the preparation, separately from the powder mixture and the water and/or the aqueous solution. In one embodiment of the invention, the phosphoric acid is orthophosphoric acid. The salt may be present in the form of its aqueous solution which is mixed as mixing liquid (i.e., aqueous component) with the dry powder mixture (i.e., powder mixture component) for the formation of the cement. For controlling the reaction rate, additional alkali salt or ammonium salt may be present in dry form in the powder mixture. For this, the powder mixture preferably contains in addition $NaH_2PO_4$ and/or $Na_2HPO_4$, $KH_2PO_4$ and/or $K_2HPO_4$ or combinations of the mentioned Na- and K-salts of the orthophosphoric acid.

As an alkali salt for the aqueous solution of the mixing liquid, a Na- and/or a K-salt of the orthophosphoric acid is particularly suitable, especially the primary or the secondary salts and particularly their combinations. In one embodiment, the alkali salt of the orthophosphoric acid includes, but is not limited to, a primary potassium salt ($KH_2PO_4$), a secondary potassium salt ($K_2HPO_4$) of the orthophosphoric acid and a mixture thereof, and a primary sodium salt ($NaH_2PO_4$), a secondary sodium salt ($Na_2HPO_4$) of the orthophosphoric acid and a mixture thereof, and combinations of the mentioned potassium and sodium salts. As an ammonium salt for the aqueous solution of the mixing liquid, $(NH_4)_2HPO_4$ is particularly suitable.

In one embodiment, for the strontium ions to be incorporated into the strontium-apatite structure in a favorable manner, the strontium is present in the powder mixture advantageously as strontium phosphate ($Sr_3(PO_4)_2$), or as strontium hydrogenphosphate ($SrHPO_4$), or a mixture thereof. The amount of $SrHPO_4$ and/or $Sr_3(PO_4)_2$ in the powder mixture is preferably more than about 10 wt.-% (weight percent) and up to about 60 wt.-%. In another embodiment, more than about 15 wt.-%, particularly more than about 20 wt.-% thereof is contained.

The optionally additional incorporated $SrCO_3$ in the powder mixture may be present in an amount of, for example, about 0.01 wt.-% to about 10 wt.-%.

The powder mixture may contain, as desired, additional suitable substances, e.g., metal carbonates, Ca-, Mg-, Sr-, Na-, K-sulfates, Ca-, Na-, K-phosphates, Ca-, Na-, K-hydrogen-phosphates as well as their oxides and/or hydroxides.

For the preparation of the strontium-apatite cement, the powder components described above are mixed with the above described aqueous component (the mixing liquid) and this mixture is subsequently allowed to be hardened, so that the strontium-apatite is formed as reaction product. Here, the powder mixture may be brought to hardening both by alkali solutions, which contain $(NH_4)_2HPO_4$, $K_2HPO_4$ and/or $Na_2HPO_4$, as well as by acid solutions, which contain $NaH_2PO_4$ and/or $KH_2PO_4$, or by means of suitable mixed solutions of the mentioned primary and secondary orthophosphates. The aqueous solution preferably has a pH value in the range of about 5 to about 12.

After mixing, a paste is usually formed. This paste can be filled into a mold, whereby after hardening of the paste conforming to the mold matrix, defined molded bodies may be prepared. Here, the viscosity and/or the consistency of the mixture can be adjusted in such a manner that it may not only be incorporated by tools into defects in the form of a paste, but may also be injected.

Embodiments of the cement preparation and the strontium-apatite cement of the present invention may be used for medical purposes and are particularly suitable as bone substitute material, as bone filler, as bone cement, as bone adhesive, and above all as a therapeutic agent for the treatment of osteoporosis.

The cement preparation and the strontium-apatite cement according to the invention are additionally suitable as supporting material for drugs of biological or pharmaceutical origin. For this, the preparation additionally contains, in the powder component and/or the aqueous liquid component, a pharmacological and/or biologically active substance, such as an antibiotic, a cytostatic agent, an analgetic agent (i.e., analgesic), a disinfectant, a growth factor, a protein or a biopolymer, or combinations of the mentioned effective substances. The use of a drug from the group of gentamicin, tobramycin, clindamycin, vancomycin, a drug from the transforming growth factor beta (TGF-β) series, or a drug from the series of bone morphogenetic proteins (BMPs), or combinations of the mentioned drugs are particularly suitable.

In one embodiment, the preparation additionally contains, in the powder component, a substance in the form of granular particles which dissolves in the aqueous liquid component, e.g., salts, sugars, or synthetic, hydrolytically decomposable polymers. These granular particles, which are used, e.g., in a grain size of 10 to 300 μm, then generate a pore system after the mixing and during the hardening process, whereby the surface area is increased and the resorption performance is accelerated.

The invention is subsequently explained in further detail by means of non-limiting examples.

EXAMPLES

In the examples, the following abbreviations are used:
M=powder mixture
L=liquid
L/M=liquid/powder-ratio in ml/g
$t_i$=initial hardening time (according to ASTM C266-89)
$t_f$=final hardening time (according to ASTM C266-89)
$C_s$(xh/yd)=pressure strength in MPa after a storage of x hours/y days in 37° C. warm 0.7% sodium chloride salt solution
MPa=mega Pascal Preparation of strontium-apatite cement preparations and cements formed thereof:

As indicated in the following examples 1 to 7, after weighing all constituents, the powder components M were homogenously ground in a ball mill and subsequently mixed with an aqueous solution L in the indicated ratio. After the lapse of a certain hardening period, the respective pressure strength was determined.

Example 1

$M$=65 g $Ca_3(PO_4)_2$+16 g $Sr_3(PO_4)_2$ $L$=3.5 M$(NH_4)_2HPO_4$ $L/M$=0.40

$C_s$(48 h)=30 MPa $C_s$(10 d)=43.8 MPa

Example 2

$M$=65 g $Ca_3(PO_4)_2$+16 g $Sr_3(PO_4)_2$ $L$=4% $Na_2HPO_4$ $L/M$=0.35

$t_i$=13'30"(13 minutes and 30 seconds)

Example 3

$M$=65 g $Ca_3(PO_4)_2$+16 g $Sr_3(PO_4)_2$+3 g $SrCO_3$ $L$=3,5 M$(NH_4)_2HPO_4$ $L/M$=0.40

$C_s$(10 d)=46.4 MPa

Example 4

$M$=60 g $Ca_3(PO_4)_2$+10 g $Sr_3(PO_4)_2$+10 g $SrHPO_4$+3 g $SrCO_3$ $L$=3M $K_2HPO_4$/1M $KH_2PO_4$ $L/M$=0.40

$C_s$(2 h)=3.8 MPa $C_s$(18 h)=26.4 MPa

Example 5

$M$=65 g $Ca_3(PO_4)_2$+16 g $SrHPO_4$+3 g $SrCO_3$ $L$=3M $K_2HPO_4$/1M $KH_2PO_4$ $L/M$=0.30

$C_s$(5 h)=18.4 MPa

Example 6

$M$=65 g $Ca_3(PO_4)_2$+12 g $Sr_3(PO_4)_2$+14 g $SrHPO_4$+3 g $SrCO_3$ $L$=3.2M$(NH_4)_2HPO_4$ $L/M$=0.35

$C_s$(5 h)=13.0 MPa

Example 7

$M = 30$ g $Ca_3(PO_4)_2 + 10$ g $Sr_3(PO_4)_2 + 10$ g $SrHPO_4 + 5$ g $SrCO_3 + 10$ g $K_2HPO_4$ $L = 3M$ $K_2HPO_4/1M$ $KH_2PO_4$ $L/M = 0.22$ $C_s(72\ h) = 40$ MPa

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the claims. All publications, patents and patent applications cited in this specification are herein incorporated by reference in their entirety.

What is claimed is:

1. A method for augmenting bone, the method comprising:
   providing a powder mixture component comprising a tricalcium orthophosphate and a strontium orthophosphate, wherein the molar ratio of calcium phosphate is 1 to about 1.5, and a molar ratio of strontium to phosphate is not greater than about 1.5 and an aqueous component comprising a solution of a salt of an orthophosphoric acid selected from the group consisting of an alkali salt, an ammonium salt and a combination thereof;
   combining the powder mixture and the aqueous component to form a bone substitute, wherein the bone substitute contains no more than trace amounts of magnesium ions; and
   delivering the bone substitute to a site in contact with a bone.

2. The method for augmenting bone according to claim 1, further comprising forming the bone substitute into a predetermined shape.

3. The method for augmenting bone according to claim 1, further comprising closing a bone defect in a patient.

4. The method for augmenting bone according to claim 1, further comprising promoting anabolic activity in the bone of a patient.

5. The method for augmenting bone according to claim 1, wherein combining the powder mixture component and the aqueous component comprises forming a paste.

6. The method for augmenting bone according to claim 5, further comprising placing the paste into a mold and allowing the paste to harden into a molded shape.

7. The method for augmenting bone according to claim 6, further comprising inserting molded shape of bone substitute into a patient to augment a bone.

8. The method for augmenting bone according to claim 1, further comprising injecting the bone substitute into a site in a bone.

9. The method for augmenting bone according to claim 1, comprising filling a gap or defect in a bone.

10. The method for augmenting bone according to claim 1, further comprising adding a biological or pharmaceutical compound.

11. The method for augmenting bone according to claim 10, wherein adding a biological or pharmaceutical compound comprises adding a drug from the series of bone morphogenic proteins.

12. The method for augmenting bone according to claim 1, further comprising adding granular particles to the powder component and dissolving the granular particles in the aqueous component.

13. The method for augmenting bone according to claim 12, wherein the granular particles are about 10 μm to about 300 μm.

14. The method for augmenting bone according to claim 1, wherein the salt of an orthophosphoric acid is a primary or secondary sodium or potassium salt.

15. The method for augmenting bone according to claim 1, comprising delivering the bone substitute as a bone adhesive to a site in contact with a bone.

16. The method for augmenting bone according to claim 1, comprising delivering the bone substitute as a bone cement to a site in contact with a bone.

17. The method for augmenting bone according to claim 1, comprising delivering the bone substitute as a bone filler to a site in a bone.

18. The method for augmenting bone according to claim 11, further comprising promoting anabolic activity in the bone.

* * * * *